United States Patent [19]
Korec

[11] Patent Number: 4,634,417
[45] Date of Patent: Jan. 6, 1987

[54] PROCESS FOR TREATMENT OF TUMORS AND APPARATUS THEREFOR

[75] Inventor: Stefan Korec, McLean, Va.

[73] Assignee: Georgetown University, Washington, D.C.

[21] Appl. No.: 748,034

[22] Filed: Jun. 24, 1985

Related U.S. Application Data

[63] Continuation of Ser. No. 447,222, Dec. 6, 1982, abandoned.

[51] Int. Cl.$^4$ ............................................. A61M 37/00
[52] U.S. Cl. ......................................... 604/4; 210/612; 210/615; 210/927; 424/85; 424/88; 424/95; 424/105; 435/174; 435/175; 435/176; 435/177; 435/178; 435/179; 435/180; 435/181; 435/883; 604/5; 604/6
[58] Field of Search ....................... 210/612, 615, 927; 260/112 B; 424/85, 88, 95, 105; 435/174-181, 883; 604/4, 5, 6

[56] References Cited

U.S. PATENT DOCUMENTS

| | | | |
|---|---|---|---|
| 3,903,262 | 9/1975 | Pappenhagen et al. | 260/112 B |
| 3,928,139 | 12/1975 | Dorn | 195/103.5 R |
| 3,994,799 | 11/1976 | Yao | 204/301 |
| 3,995,018 | 10/1976 | Sjoquist | 435/7 |
| 4,059,685 | 11/1977 | Johnson | 424/12 |
| 4,215,688 | 8/1980 | Terman | 128/214 R |
| 4,223,672 | 9/1980 | Terman | 128/214 R |
| 4,261,828 | 4/1981 | Brunner et al. | 210/287 |
| 4,350,156 | 9/1982 | Malchesky et al. | 128/214 R |
| 4,379,083 | 4/1983 | Falke et al. | 260/112 B |
| 4,381,004 | 4/1983 | Babb | 128/214 R |
| 4,384,993 | 5/1983 | Sato et al. | 260/112 B |
| 4,409,330 | 11/1983 | Pollard | 435/178 |
| 4,410,660 | 10/1983 | Straus | 525/54.1 |
| 4,430,318 | 2/1984 | Langone | 424/1.1 |
| 4,438,198 | 3/1984 | Schmer | 435/178 |
| 4,450,153 | 5/1984 | Hopkins | 424/94 |

OTHER PUBLICATIONS

BIO-RAD, Price List J, Jan. 1984, "Chromatography Electrophoresis Immunochemistry HPLC", pp. 45-53.

Primary Examiner—Lucille M. Phynes
Attorney, Agent, or Firm—Oblon, Fisher, Spivak, McClelland, & Maier

[57] ABSTRACT

A process for removing immunosuppressive substances from the blood serum of cancer patients comprises contacting the serum at a temperature below room temperature and preferably not greater than 5° C., with Protein A of S. aureus immobilized on a substrate. Conducting the immunoabsorption at low temperature reduces the amount of anaphylatoxins produced in the process and thereby reduces the side effects of immunoperfusion treatment. An apparatus for low-temperature immunoperfusion treatment comprises a chamber for containing the immunoabsorbent, inlet and outlet tubes connected to the chamber, and a cooling jacket surrounding the chamber and at least a portion of the inlet tube.

23 Claims, 2 Drawing Figures

PROCESS FOR TREATMENT OF TUMORS AND APPARATUS THEREFOR

This is a continuation of application Ser. No. 447,222, filed Dec. 6, 1982, now abandoned.

BACKGROUND OF THE INVENTION

1. Field of the Invention

This invention relates to the in vivo treatment of tumors and more particularly to treating tumors by removing immunoglobulins and immune complexes from the blood of patients afflicted with malignant tumors. The invention also relates to apparatus for removing these immunoglobulins and immune complexes.

2. Description of the Prior Art

In patients with cancer, it is known that there are soluble immunosuppressive substances in the blood serum which interfere with the ability of the leukocytes to attack and destroy the tumor cells. These "blocking factors" seem to develop in the early stages of tumor growth and have been demonstrated to be present in sera of animals and humans with growing tumors. It has also been found that Protein A (SpA), which is found in the cell wall of *Staphylococcus aureus* can absorb these "blocking factors" from the sera of animals and patients bearing actively growing tumors. The use of killed *S. aureus* containing Protein A in order to remove immunoglobulins containing blocking activity from the blood of cancer patients for therapeutic purposes was suggested by G. Steele, Jr. et al, Int. T. Cancer 15:180, 1975. Treatment of tumors in cancer patients by immunoadsorption of proteins from their blood serum by contacting the serum with immobilized Protein A has been reported by Bansal, S. C., et al, Cancer 1978, Vol. 42 pp. 1-18; Terman, D. S., et al, New England Journal of Medicine 1981, Vol. 305, pp. 1195-1200; Ray, P. K., et al., Cancer 1982, Vol. 49, pp. 1800-1809; and Bensinger, W. I., International Cancer Meeting Abstracts, Seattle, September 1982. In these treatments, blood was continuously withdrawn from the patient, the cellular components were separated from the serum, the serum was passed over immobilized Protein A, the serum was recombined with the cells and the blood was reinfused.

The methods of immobilizing the Protein A in these treatments included using killed *S. aureus* having Protein A as a constituent of the cell wall, immobilizing the Protein A in a matrix of charcoal and collodion, and covalently binding the Protein A to the surface of crystalline silica. In each case the immunoadsorption treatment was apparently conducted with the immunoadsorbent at room temperature.

In each case some regession of the tumors in at least some of the patients treated was reported. However, in each case the treatments were also accompanied by side effects such as fever, chills, hypotension, tachycardia and bronchospasm. In some instances, therapeutic intervention was required to control these side effects.

Hence, a need has continued to exist for a method of removing cytotoxicity-inhibiting substances from the blood serum of cancer patients which avoids the side effects of the known procedures.

SUMMARY OF THE INVENTION

Accordingly, it is an object of this invention to provide a method for removing cytotoxicity-inhibiting components from the serum of cancer patients.

A further object is to provide an immunoperfusion procedure for removing cytotoxicity-inhibiting materials from the blood of cancer patients.

A further object is to provide an apparatus for treating cancer patients by immunoperfusion.

A further object is to provide a procedure for treating cancer patients by immunoadsorption of proteins from blood which minimizes side effects.

Further objects of the invention will become apparent from the description of the invention which follows.

The objects of the inventions are attained by (1) removing serum from the cancer patient, (2) contacting said serum with Protein A immobilized on a solid substrate, whereby cytotoxicity-inhibiting materials are removed from said serum, and (3) returning the serum to the patient after the contacting step, wherein said contacting in step two is conducted at a temperature sufficiently below body temperature to avoid unnecessary activation of complement.

An apparatus suitable for carrying out this process on a continuous basis comprises a chamber containing particles of a solid support on which Protein A is immobilized, inlet and outlet tubes for conducting the serum to the chamber and removing it therefrom, and a jacket for a cooling medium surrounding said chamber.

DETAILED DESCRIPTION OF THE INVENTION AND PREFERRED EMBODIMENTS

It is believed that the side effects of immunoperfusion are caused by the products of complement activation. These products, commonly known as anaphylatoxins, are believed to be responsible for the hypotension, bronchospasm and tachycardia which have been observed in patients undergoing immunoperfusion therapy. In this therapy blood is continuously removed from the patient, the plasma is separated from the red blood cells and passed through an immunofilter where it contacts an immunoabsorbent which removes from the serum the undesirable components. The plasma is then recombined with the blood cells and returned to the patient. However, in the course of the treatment of the blood serum by this process some undesirable activation of the complement system is produced, which leads to the generation of anaphylatoxins and the accompanying side effects in the patient. According to the invention, the generation of anaphylatoxins is reduced by carrying out the contact of the serum with the immunoabsorbant at a reduced temperature. Contacting the serum with the immunoabsorbant at temperatures below the body temperature of the patient being treated and in particular below room temperature, reduces the amount of anaphylatoxins; however, it is preferable to contact the serum with the immunoabsorbant at the lowest possible temperature. Accordingly, it is preferable to keep the immunoabsorbant at a temperature of less than 5° C. and more preferably at 0° C.

In certain cases, however, a certain amount of complement activation may be desirable in treatment of the patient. Therefore, it is within the scope of this invention to conduct the immunoperfusion at a temperature which permits only the desired amount of complement activation and to regulate the temperature of the immunoperfusion for this purpose.

Figure 1:
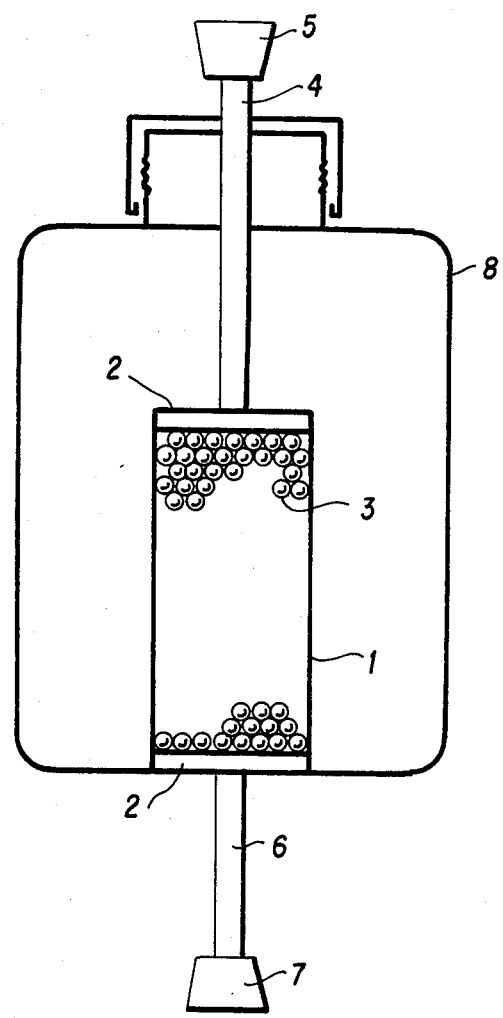
FIG. 1 illustrates one embodiment of the perfusion filter of the invention.
Figure 2:
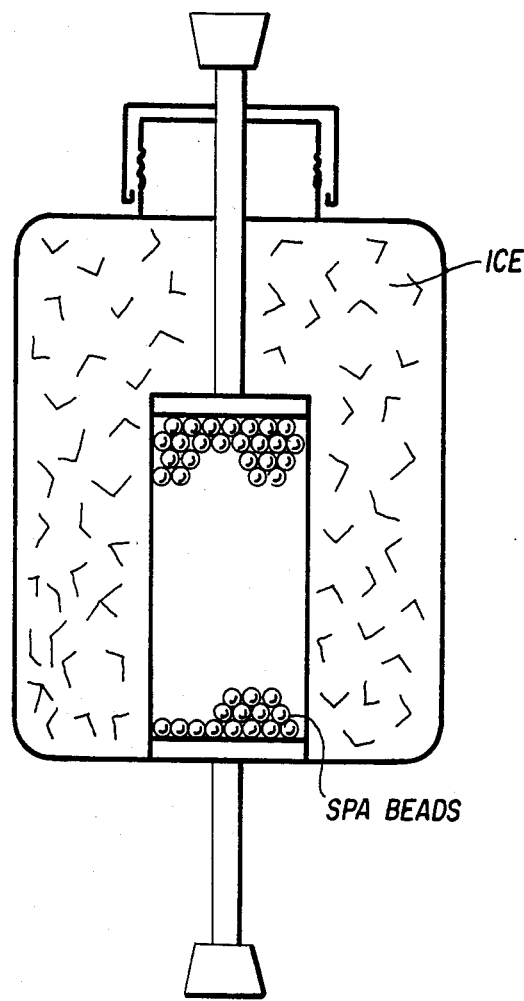
FIG. 2 illustrates the immunoperfusion apparatus of the present invention packed with ice.

An apparatus for carrying out the process of this invention, a preferred embodiment of which is illustrated in FIG. 1, comprises an elongated cylindrical chamber 1, provided with closures 2 at each end thereof and packed with glass beads 3 coated with a polyacrylamide resin upon the surface of which Protein A is immobilized by covalent bonding thereto. The serum to be subjected to the immunofiltration is supplied to the apparatus through inlet tube 4 provided with connection 5 for connecting the inlet tube to the other tubes of the perfusion apparatus. The treated serum leaves the immunofiltration chamber through outlet tube 6, fitted with connecting device 7. The chamber containing the immobilized Protein A is surrounded by a jacket 8 which contains a cooling medium to keep the serum at a low temperature while the immunofiltration process takes place. Since the jacket also surrounds a portion of the inlet tube 4, it provides for precooling of the serum before it is subjected to the immunofiltration process. In a preferred embodiment of the method of this invention, the cooling jacket is packed with ice to assure that the immunofiltration is conducted at or very near to 0° C.

Having generally described the invention, a more complete understanding can be obtained by reference to certain specific examples, which are provided herein for purposes of illustration only and are not intended to be limiting unless otherwise specified.

EXAMPLE 1

Preparation of glass beads coated with Protein A

Seven grams of a mixture of acrylamide and N,N'-methylene-bis-acrylamide (ratio 19:1) were dissolved in 100 ml of double distilled water and mixed for one hour with a magnetic stirrer. One gram of an ion exchange resin (Amberlite MB1) was added to neutralize any acrylic acid present and the solution was filtered. Ten milliliters of glycerol and 0.1 ml of TEMED (polymerization initiator) were then added to the solutions and the solution was thoroughly mixed. Thereupon, 1.0 ml of an aqueous solution of ammonium persulfate (22.8 mg. ml) was admixed to initiate polymerization. Immediately, 4 mm diameter glass beads which had been cleaned by agitation for 24 hours in a 1N hydrochloric acid solution, washed 10 times with distilled water and dried were mixed with the solution. Portions of the bead-solution mixture were placed into 50 ml screw cap tubes and agitated on an orbital mixer for 10 hours to assure even coating of the beads with the polymer. The beads were then spread on a siliconized glass surface and the polymerization was allowed to proceed for another 6 hours. The polyacrylamide coated beads were then washed 10 times with distilled water.

A quantity of the coated beads, in a suitable container, were just covered with distilled water, an equal volume of hydrazine hydrate was added, and the container was tightly covered and placed in a water bath at 47° C. After 45 minutes the beads were washed 3 times with 0.1M sodium chloride and three times with 0.3N hydrochloric acid. The beads were cooled to 4° C. in the 0.3N HCl solution, 1M sodium nitrite solution was added in the ratio of 1 ml for each 15 ml of the acid solution, and the mixture was incubated for 20–30 minutes at 4° C. The solution was then drained and the beads were washed once with 0.3N HCl and three times with 0.1M sulfamic acid, and therafter extensively washed with distilled water. The beads were then added to a solution containing the desired amount of Protein A dissolved in cold 0.1M sodium tetraborate and the mixture was stirred at 4° C. for 12–24 hours. The solution was drained and the beads were convered with a 1M solution of ammonium chloride and incubated with agitation for 2 hours at room temperature to convert all the unreacted azide groups back to the neutral amide groups. The beads were then washed extensively with distilled water and packed into a plastic column, flushed with distilled water radiation sterilized and stored at 4° C.

EXAMPLE 2

In order to illustrate the decreased activation of complement produced by the process of this invention, human plasma was subjected to immunoperfusion over Protein A, at room temperature and at a low temperature approaching 0° C. Human plasma was passed through an immunofilter of the type illustrated in the drawing, packed with the Protein A coated beads prepared by the procedure of Example 1. One sample was subjected to perfusion at room temperature, i.e., with the jacket of the filter empty, and a second sample was subjected to perfusion at low temperature, i.e., with the filter packed with ice. The amount of certain complement fractions in the serum was determined before and after perfusion for each case by conventional radioimmunoassay (RIA) procedures. The number of counts of radioactive decompositions for the total hemolytic activity of complement (CH-50) and for a number of fractions of complement (C-3, C-4, and C-5), which is a measure of the amounts of these ingredients present in the serum, are tabulated in Table 1.

TABLE 1

| Temperature | | Amounts of Complement Factors | |
|---|---|---|---|
| | | Before Perfusion | After Perfusion |
| Room Temperature | CH-50 | 17 | 8 |
| | C-3 | 17,606 | 10,213 |
| | C-4 | 121,813 | 88,788 |
| | C-5 | 146,430 | 38,196 |
| Ice Temperature | CH-50 | 18 | 16 |
| C-3 | 30,073 | 22,825 | |
| | C-4 | 94,109 | 65,540 |
| | C-5 | 154,119 | 131,148 |

It can be seen from an inspection of the data in Table 1 that the amount of complement in the serum after perfusion at room temperature is considerably less than that present before perfusion, which indicates that a substantial portion of the complement has been activated. On the other hand, in the perfusion at ice temperature, relatively little of the complement was activated. Inasmuch as it is generally believed that the activation of complement is associated with the production of anaphylatoxins which lead to the side effects observed in in vivo immunoperfusion, these results indicate that fewer side effects would be expected when the immunoperfusion is conducted at low temperature.

EXAMPLE 3

In order to confirm that fewer side effects are produced by immunoperfusion at low temperature, in vivo experiments were conducted as follows.

Three shorthaired German pointer dogs, surgically prepared with carotid-vein shunts for access to the circulatory system, were treated by immunoperfusion. Blood was continuously withdrawn from the animal, the cells were separated from the plasma by conventional techniques and the plasma was passed through an immunoperfusion filter. The plasma was then recombined with the cell fraction and the whole blood was reinfused into the animal. Room temperature perfusion was conducted using a perfusion filter packed with whole, killed *Staphylococcus aureus* having Protein A on the cell wall. During the room temperature perfusion, the dogs exhibited signs of discomfort and did not engage in normal activity.

The perfusion experiments were then repeated using the same dogs, but using instead the immunoperfusion filter of this invention packed with the Protein A covered beads prepared as in Example 1 and with the jacket of the filter packed in ice. During the perfusion at low temperature, the dogs behaved essentially normally, and exhibited fewer signs of discomfort than in the room temperature perfusion experiment.

EXAMPLE 4

This example illustrates the treatment of tumors in human patients.

Two patients were selected for immunoadsorption therapy, one having malignant melanoma and the other having an inoperable carcinoma of the colon.

In the patient having colon carcinoma, the tumor had recurred after an initial resection and chemotherapy had failed. In the patient having melanoma, surgery and chemotherapy had also failed to eliminate the tumor.

Immunoadsorption therapy was performed by withdrawing blood from a vein, passing the blood through a centrifugal cell separator to produce a cell fraction and a plasma fraction, passing the plasma fraction through the immunoadsorption filter of this invention in its ice-filled jacket, rewarming the plasma to 37° C., recombining the plasma fraction with the cell fraction, and reinfusing the whole blood into a vein.

The patient having colon carcinoma was treated twice weekly for two weeks, then once weekly for two weeks. In the initial treatment 300 ml of plasma were passed through the immunoperfusion filter which contained 15 mg of immobilized SpA. The amount of plasma perfused and the amount of SpA were increased gradually in successive treatments until a total of 1300 ml of plasma was perfused using 100 mg of SpA.

The procedure produced only minimal symptoms of toxicity, a slight elevation of temperature (to 38.5° C.) and a transient slight decrease of blood pressure, neither symptom requiring therapeutic intervention. Substantial immunologic changes were observed. A marked decrease in the concentration of immunoglobulins in the perfused plasma was observed. The decrease of different classes of immunoglobulins (Ig) was not always uniform. In some instances IgG was preferentially removed and in others IgM or IgA was preferentially removed. The decrease amounted up to 50% for IgG. A decrease in the concentrations of C-3 and C-4 complement fractions was also observed. Absolute lymphocyte count increased by 50-100% during immunoperfusion, then decreased to the pretreatment level over the following 48 hours.

The concentration of carcinoembryonic antigen (CEA) in the plasma decreased from 140 ng/ml to 30 ng/ml in the course of the treatment. The concentration of CEA in the plasma is a marker for colon carcinoma, and the decrease in the concentration thereof in this clinical setting is indicative of partial regression of the tumor. After 4 weeks the patient was improved in general health, had gained 10 pounds, and was able to return to work.

The patient having malignant melanoma had three separate tumors on the chest wall and was given a similar course of treatment. Side effects were again minimal and included a slight inflammation at the base of the melanoma. However, one of the tumors began to grow and, accordingly, the treatment had to be discontinued.

Having now fully described the invention, it will be apparent to one of ordinary skill in the art that many changes and modifications can be made thereto without departing from the spirit of scope of the invention as set forth herein.

What is claimed and intended to be secured by Letters Patent of the United States is:

1. A process for removing cell mediated cytotoxicity-inhibiting substances from the blood of patients having cancer comprising:
   (1) removing the blood from the patient;
   (2) separating plasma and red blood cells from said blood;
   (3) cooling said plasma to between 0° and 5° C. to prevent undesired side effects;
   (4) contacting said plasma with Protein A immobilized on a solid support formed of polyacrylamide to remove said substances;
   (5) recombining said plasma with said red blood cells; and
   (6) returning the plasma to said patient.

2. The process of claim 1 wherein said contacting step (4) is carried out at a temperature not greater than 5° C.

3. The process of claim 1 wherein said contacting step (4) is carried out at a temperature of about 0° C.

4. The process of claim 1 wherein said process is conducted continuously.

5. A perfusion apparatus for removing cell-mediated cytotoxicity-inhibiting substances from the blood plasma of cancer patients comprising:
   a chamber substantially filled with solid support particles formed of polyacrylamide, the surface of said particles having Protein A immobilized thereon;
   means for introducing plasma into said chamber;
   means for withdrawing plasma from said chamber; and
   a cooling jacket means surrounding said chamber;
   said cooling jacket means maintaining the temperature of the chamber at between about 0° to 5° C.

6. The perfusion apparatus of claim 5 wherein said means for introducing plasma into said chamber comprises a tubular fluid transmissive conduit in fluid transmissive communication with the interior of said chamber.

7. The perfusion apparatus of claim 5 wherein said means for removing plasma from said chamber is a tubular fluid transmissive conduit in fluid communication with the interior of said chamber.

8. The perfusion apparatus of claim 6 wherein at least a portion of said conduit lies within said cooling jacket.

9. The perfusion apparatus of claim 5 wherein said chamber has the shape of a right circular cylinder having a first base and a second base, said means for introducing plasma into said chamber is a fluid-transmissive tubular conduit in fluid transmissive communication with the interior of said chamber and attached thereto at said first base of said cylinder, and said means for removing plasma from said chamber is a fluid-transmissive tubular conduit in fluid transmissive communication with the interior of said chamber and attached thereto at said second base of said cylinder.

10. The perfusion apparatus of claim 9, wherein said fluid transmissive fluid conduit for introducing said plasma into said chamber lies at least partially within said cooling jacket.

11. A perfusion apparatus for low temperature perfusion treatment of biological fluids comprising:
a chamber adapted to contain in its interior an immunoabsorbent,
an inlet tube in fluid-transmissive communication with the interior of said chamber;
an outlet tube in fluid-transmissive communication with the interior of said chamber;
a cooling jacket means surrounding said chamber and at least a portion of said inlet tube; wherein said cooling jacket means maintaining said chamber is at between about 0° and 5° C.

12. The process of claim 1, wherein the solid support is in the form of particles having said Protein A immobilized on the surfaces thereof.

13. The apparatus of claim 5 wherein the particles are beads.

14. The process of claim 1, wherein the polyacrylamide is coated on the solid support, and wherein the Protein A is immobilized by covalent bending thereto.

15. The process of claim 1 wherein the solid support is glass.

16. The apparatus of claim 5, wherein the polyacrylamide is coated on the solid support, and wherein the Protein A is immobilized by covalent bending thereto.

17. The apparatus of claim 16 wherein the solid support is glass.

18. The apparatus of claim 11 wherein the chamber is substantially filled with the immunoadsorbant; said imminoadsorbent being a solid support having protein A immobilized on the surface thereon.

19. The apparatus of claim 18 wherein the solid support is formed from polyacrylamide.

20. The apparatus of claim 19 wherein the polyacrylamide is coated on the solid support.

21. The process of claim 12, wherein said particles are beads.

22. The process of claim 1, wherein said undesired side effects are those resulting from the production of anaphylotoxins.

23. The process of claim 22, wherein said side effects comprise fever, chills, hypotension, tachycardia and bronchospasm.

* * * * *